United States Patent
Sakaguchi et al.

(10) Patent No.: US 8,661,913 B2
(45) Date of Patent: Mar. 4, 2014

(54) METHOD OF MEASURING STRESS HISTORY AND COMPOSITE MATERIAL CONTAINING CEMENT AS MAIN COMPONENT

(75) Inventors: Arito Sakaguchi, Kanagawa (JP); Hide Sakaguchi, Kanagawa (JP)

(73) Assignee: National University Corporation Nagaoka University of Technology, Niigata (JP)

( * ) Notice: Subject to any disclaimer, the term of this patent is extended or adjusted under 35 U.S.C. 154(b) by 188 days.

(21) Appl. No.: 13/129,744

(22) PCT Filed: Nov. 17, 2008

(86) PCT No.: PCT/JP2008/070847
§ 371 (c)(1),
(2), (4) Date: May 17, 2011

(87) PCT Pub. No.: WO2010/055584
PCT Pub. Date: May 20, 2010

(65) Prior Publication Data
US 2011/0232394 A1    Sep. 29, 2011

(51) Int. Cl.
*G01N 3/00* (2006.01)
(52) U.S. Cl.
USPC .......................................................... 73/803
(58) Field of Classification Search
USPC .................................... 73/760, 774, 803
See application file for complete search history.

(56) References Cited

U.S. PATENT DOCUMENTS

| | | | | |
|---|---|---|---|---|
| 5,690,729 | A * | 11/1997 | Jones, Jr. ..................... | 106/682 |
| 8,066,812 | B2 * | 11/2011 | Wu et al. ..................... | 106/685 |
| 2009/0272052 | A1 * | 11/2009 | Eide et al. ..................... | 52/251 |
| 2009/0286076 | A1 | 11/2009 | Xu et al. | |
| 2009/0301355 | A1 * | 12/2009 | Eide ............................. | 106/737 |

FOREIGN PATENT DOCUMENTS

| | | |
|---|---|---|
| JP | 11-295198 | 10/1999 |
| JP | 2004-101322 | 2/2004 |
| JP | 07-063624 | 3/2007 |
| JP | 2008/268123 | 6/2008 |
| JP | 2008-268123 | 11/2008 |
| JP | 2008-286689 | 11/2008 |
| WO | 2007/015532 | 2/2007 |
| WO | 2007015532 | 2/2007 |

OTHER PUBLICATIONS

International Search Report of the Authorized Searching Authority (corresponding to priority application: EP08878130); European Patent Office; Issued May 10, 2012; (5 pages).
K.J. Rowe and E.H. Rutter. "Palaeostress Estimation Using Calcite Twinning: Experimental Calibration and Application to Nature." Published in Journal of Structural Geology, vol. 12, No. 1. Geology Department, Imperial College, University of London, London, SW7 2BP, U.K.; pp. 1-17 (1990).
International Search Report from Corresponding Application: PCT/JP2008/070847; Japanese Patent Office Searching Authority; Authorized Officer Chang Soo Han; Issued Dec. 22, 2008; (4 pages—2 in Japanese; 2 in English).
Written Opinion from Corresponding Application: PCT/JP2008/070847; Japanese Patent Office Searching Authority; Authorized Officer Chang Soo Han; Issued Jun. 15, 2011; (5 pages in English).

* cited by examiner

*Primary Examiner* — Max Noori
(74) *Attorney, Agent, or Firm* — Benesch, Friedlander, Coplan & Aronoff, LLP

(57) ABSTRACT

There are provided a method by which a stress history of an object can be measured with high reliability if the object, which has temporarily been elastically deformed upon receiving an external force, recovers from the elastic deformation, and a composite material containing cement as a main component, of which a stress history can be measured with high reliability without reducing the strength of the material itself and without breaking the structure. To achieve the above-mentioned advantages, the method includes the steps of: acquiring an initial value of a twin density for calcite particles contained in an object to be measured that is elastically deformable upon receiving an external force; and measuring a history of stresses received by the object to be measured on the basis of a difference from the initial value in respect of the twin density for the calcite particles after the object to be measured receives the external force. The composite material includes calcite particles, for which a twin density is known and which are mixed to be distributed in the material, partially replacing an aggregate of the material.

7 Claims, No Drawings

METHOD OF MEASURING STRESS HISTORY AND COMPOSITE MATERIAL CONTAINING CEMENT AS MAIN COMPONENT

TECHNICAL FIELD

The present invention relates to a method of measuring a stress history and a composite material containing cement as a main component.

BACKGROUND ART

Conventionally, for example, a marker or a sensor is provided at a concrete product or structure or the like and then an existing stress is measured to obtain a measurement of an internal stress in the concrete (as disclosed in Patent Document 1) or an internal stress in a concrete product or structure or the like is estimated based on the rebound amount or the AE Kaiser effect of a core extracted from the concrete (as disclosed in Patent Documents 2 and 3).

Patent Document 1: Japanese Patent Application Publication No. 2004-101322
Patent Document 2: Japanese Patent Application Publication No. 11-295198
Patent Document 3: Japanese Patent Application Publication No. 07-63624

DISCLOSURE OF INVENTION

Technical Problem

If a concrete structure is not broken but elastically deformed when a concrete structure, for example, has been subjected to the momentary significant force due to a natural disaster such as an earthquake and a whirlwind or an accident such as a collision between the concrete structure and a high-speed traffic entity, and thereafter an external force is released and the elastic deformation is recovered, the magnitude and distribution of the force received by the concrete structure may not accurately be known.

In such a case, a stress history of the concrete structure may be analyzed by estimation through simulation or by estimation of the maximum stress amount of a core extracted from a point of the concrete structure that is expected to be important, using an acoustic emission (AE) measurement. By either method, however, the stress history may not be evaluated with high reliability.

In the estimation through simulation, the magnitude and the direction of the external force, which abruptly occurred, are obtained only through guessing, and thus the simulation results may be ambiguous.

In the estimation through the AE measurement, a core material is loaded on a mechanical testing machine to obtain the AE of a minute breaking sound, and the maximum stress is estimated on the basis of a point in the AE at which the minute breaking sound increases. By this method, however, an accurate estimation cannot be expected. In addition, the AE measurement is not a reproduction test because the direction of the maximum stress at the occurrence of the event is not known. Moreover, because the AE measurement is performed by a destructive inspection, the inspection may not be performed at many points in the entire structure.

Further, another method may be to analyze a stress history of a concrete structure by providing many strain gauges in the entire concrete structure for continuous monitoring. However, such a method is not practical for ordinary buildings. In addition, embedding sensors, which are foreign objects, in a concrete structure makes the structure inhomogeneous, which may cause a break of the structure.

In view of the foregoing circumstances, the inventors made diligent studies to find that changes in twin density of calcite in a composite material such as concrete exhibits a characteristic distribution that may serve as an index of a stress, and that a stress history can be analyzed on the basis of a measurement of the twin density of the calcite. The present invention was made on the basis of this finding.

An object of the present invention is to provide a method by which a stress history can be measured with high reliability if an object, which has temporarily been elastically deformed upon receiving an external force, recovers from the elastic deformation.

Another object of the present invention is to provide a composite material containing cement as a main component, of which a stress history can be measured with high reliability without reducing the strength of the material itself and without breaking the object.

Solution to Problem

A method of measuring a stress history according to the present invention comprises the steps of: acquiring an initial value of a twin density for calcite particles contained in an object to be measured that is elastically deformable upon receiving an external force; and measuring a history of stresses received by the object to be measured on the basis of a difference from the initial value in respect of the twin density for the calcite particles after the object to be measured receives the external force.

In the method of measuring a stress history according to the present invention, the initial value of the twin density for the calcite particles may be acquired since the calcite particles for which a twin density is known are mixed in advance to be distributed in the object to be measured.

In the above case, the calcite particles having the known twin density preferably do not contain twin crystals.

The method of measuring a stress history according to the present invention may further include the steps of: defining at least one area of the object to be measured as an area to be inspected and calculating an average value of the respective twin densities for a plurality of calcite particles each having a crystal face exposed on the area to be inspected to obtain an average twin density; and estimating the magnitude and distribution of the external force which has acted on the entire object to be measured on the basis of a difference between the initial value and the average twin density.

A composite material containing cement as a main component, according to the present invention, includes calcite particles for which a twin density is known and which are mixed to be distributed in the material, partially replacing an aggregate of the material.

Effect of the Invention

According to the method of the present invention, twin crystals generated in accordance with the external force which has acted on the object to be measured (for example, concrete) remain in the calcite particles even after the external force is released and the object to be measured itself recovers from the elastic deformation. Thus, the stress history, specifically the absolute values of stresses including the maximum stress, the currently existing stress, and the momentary stress, and the distribution of the stresses, for example, can be measured with high accuracy on the basis of a difference from an initial value, which should be acquired in advance, in respect of the twin density for the calcite particles.

In addition, the stress history of the entire object to be measured can be estimated by utilizing the fact that the average twin density for a plurality of calcite particles existing in an area of a predetermined size exhibits a characteristic distribution that the average twin density tends to increase according to the external force. Thus, the stress history can be detected for a multiplicity of scales ranging from a microscopic scale to a scale of the entire object to be measured such as a concrete structure, for example. A local phenomenon at an end of a crack can also be analyzed.

Further, it is only necessary to perform a surface treatment that does not affect the strength of the object to be measured itself. Thus, the measurement itself does not affect the measurement results. In addition, the measurement can be performed in a non-destructive manner, continuous observations such as a secular change, and comparison between before and after occurrence of an accident, can also be performed.

Furthermore, when calcite particles that do not initially contain twin crystals (that is, the initial value of the twin density for the calcite particles is 0) are used, a sufficiently wide measurable range is obtained, and it is not necessary to count twin crystals in an area to be measured on which no stress has acted. Thus, high efficiency is obtained.

The composite material containing cement as a main component according to the present invention, on which the above-mentioned method can be performed, is mixed with calcite particles which are foreign matters. The calcite particles have such property that they plastically flow (to form twin crystals) upon receiving a shearing force of a certain magnitude and are compatible with cement in an environment at a normal (low) temperature. When using the composite material of the present invention, it is possible to measure the stress history of a product or a structure made of the composite material without reducing the strength of the product or the structure itself due to the presence of the calcite particles in the product or structure, and without breaking the product or the structure.

BEST MODE FOR CARRYING OUT THE INVENTION

An embodiment of the present invention will be described below assuming, for example, that a stress history of a product (object to be measured) is to be measured wherein the product is made of concrete as a composite material containing cement as a main component.

In carrying out the method of the present embodiment of the present invention, it is necessary to prepare the concrete that includes calcite particles. The calcite particles are crystalline particles that exhibit twin crystals upon receiving a force including a shearing force of a certain magnitude. The calcite particles should be mixed in advance to be substantially uniformly distributed, and the initial value of the twin density for the calcite particles should be known. Such concrete is obtained by partially replacing sand as an aggregate with such calcite particles during production of the concrete. The term "twin density" refers to the number of twin crystals contained per predetermined length in an axial direction that is orthogonal to an e surface where twin crystals are generated upon receiving a shearing force of a certain magnitude.

The calcite particles are not specifically limited as long as they have a known twin density. However, the calcite particles preferably do not contain twin crystals (that is, they preferably have a twin density of 0). This is because high efficiency can be obtained as follows: a sufficiently wide measurable range (allowance for changes in the twin density) is secured in view of the measurement principle that changes in twin density are detected, and furthermore it is not necessary to count twin crystals in an area to be measured on which no stress has acted. Thus, high efficiency is obtained.

The particle diameter of the calcite particles is preferably the same as the particle diameter of the sand as the aggregate forming the concrete, and may be specifically 63 to 2000 μm, for example. The term "particle diameter of the calcite particles" refers to the short side of a rectangle circumscribed around the maximum projection area of the calcite particle.

If the particle diameter of the calcite particles is too large, the resulting concrete product or structure is not likely to have a sufficient strength. If the particle diameter of the calcite particles is too small, it may be difficult to measure the twin density on a crystal face.

The calcite particles preferably account for 0.3 to 10% by volume of the total, for example, and more preferably 1 to 5% by volume. This ensures measurement (inspection) of stresses over an intended period while positively preventing a reduction in strength of the concrete product or structure.

If the concrete in which the calcite particles are mixed as described above is subjected to an external force including a shearing force that does not break a concrete product or structure itself made of the concrete but that elastically deforms the concrete product or structure, for example, twin crystals are formed on some crystal faces of the calcite particles. The twin crystals formed on the calcite particles do not disappear even after the external force is released and the elastic deformation is recovered. Therefore, a history of stresses received by the concrete product or structure can be measured by measuring changes in twin density for the calcite particles because the calcite particles may function as a whole to be a micro stress meter.

An example of the method of measuring a stress history will be specifically described. First, a part of the surface of a thin concrete test specimen cut out from an object to be measured is selected as an area to be inspected, or a part of the surface of the object to be measured is selected as an area to be inspected without being cut out from the object to be measured as a test specimen. The surface of the area to be inspected is ground to expose respective crystal faces of a plurality of calcite particles as surfaces to be inspected. The size of the area to be inspected is not specifically limited, and may be appropriately set in accordance with the purpose.

Then, the entire surface to be inspected is scanned using an optical microscope, for example, and image analysis is performed to measure the twin density for each of the plurality of calcite particles, the crystal face of which has been exposed to allow checking whether twin crystals are present or absent. The average value of the respective twin densities thus obtained for the plurality of calcite particles, or the average twin density, is calculated.

As discussed above, the average twin density for the plurality of calcite particles, which exist in the area to be inspected having a predetermined size, depends on the magnitude of the external force, and tends to increase as the external force becomes larger. Specifically, the average twin density is proportional to the magnitude of the external force. Thus, the absolute values and distribution of the stresses received by the entire object to be measured can be estimated on the basis of a change in twin density, specifically a difference between the average twin density thus obtained and the initial value of the twin density (for example, 0).

Therefore, according to the above method, twin crystals generated due to and according to the external force which has acted on the object to be measured (for example, concrete)

remain in the calcite particles even after the external force is released and the object to be measured itself recovers from the elastic deformation. Thus, the stress history, specifically the absolute values of stresses including the maximum stress, the currently existing stress, and the momentary stress, and the distribution of the stresses, for example, can be measured with high accuracy on the basis of changes in twin density or a difference from the acquired initial value with respect to the twin density for the calcite particles.

In addition, the stress history of the entire object to be measured can be estimated by utilizing the fact that the average twin density for a plurality of calcite particles existing in an area of a predetermined size exhibits a characteristic distribution that the average twin density tends to increase according to the external force. Thus, the stress history can be detected for a multiplicity of scales ranging from a microscopic scale to a scale of the entire object to be measured such as a concrete structure, for example. A local phenomenon at an end of a crack can also be analyzed.

Further, it is necessary only to perform a surface treatment to such an extent that the measurement does not affect the strength of the object to be measured itself. Thus, the measurement itself does not affect the measurement results. In addition, the measurement can be performed in a non-destructive manner. Accordingly, continuous observations such as a secular change, comparison between before and after occurrence of an accident, or the like, for example, can also be performed.

Moreover, when calcite particles that do not initially contain twin crystals (that is, the initial value of the twin density for the calcite particles is 0) are used, a sufficiently wide measurable range is obtained, and it is not necessary to count twin crystals in an area to be measured on which no stress has acted. Thus, high efficiency is obtained.

An exemplary experiment was performed as described below to demonstrate the effect of the present invention.
<Exemplary Experiment>

High-strength mortar was produced by kneading (cement+silica fume), (sand+calcite particles), and water at a mass ratio of 1:2.5:0.35. The proportion of the silica fume was 10% with respect to the mass of the cement. The calcite particles were obtained by cutting a calcite block that does not contain twin crystals into particles having a diameter of 1.6 to 2 mm (which are as large as sand particles), and were added in a proportion of 1% with respect to the mass of the sand.

The high-strength mortar thus obtained was formed into a sample, which was matured in water at 20° C. Then, the bending strength and the compressive strength of the sample at the material age of 28 days were measured. In the bending strength test, the maximum load was 4905.0 [N] (0.5 [t]), and the bending strength was 11.5 [N/mm$^2$]. In the compressive strength test, the maximum load was 131454.0 [N] (13.4 [t]), and the compressive strength was 82.2 [N/mm$^2$].

The bending strength test was performed in accordance with JIS R 5201, and the compressive strength test used a formed sample of 4×4×8 cm.

The twin density (initial value) for the calcite particles in the sample formed from the high-strength mortar having the physical properties described above was measured in an unloaded state. The measured twin density was substantially 0/mm. The twin density was measured by defining a part of the area of the sample as an area to be inspected, grinding the surface of the area to be inspected to expose respective crystal faces of a plurality of calcite particles, and measuring the respective twin densities for the calcite particles using an optical microscope to calculate an average value.

Then, a load of about 60% of the breaking strength was applied to the sample in the same way as in the above compressive strength test, and thereafter the respective twin densities for the calcite particles in the identical area to be inspected were measured. The measured twin density (an average value of three particles) was 2.1/mm. Meanwhile, a load of the breaking strength was applied to the sample (to break the sample), and thereafter the respective twin densities for the calcite particles were measured. The measured twin density (an average value was 21.3/mm. It was confirmed that the average value of the twin densities increased in proportion to the load applied to the sample.

While an embodiment of the present invention has been described above, the present invention is not limited to the above embodiment, and may be modified in various ways.

For example, the method according to the present invention is applicable to any object to be measured that may contain calcite particles, which may specifically be a material (composite material) for construction of the building or the like, which contains cement as a main component such as mortar, a mudsill (a structure formed by packing soil) forming a foundation of a building, a molded resin article, or the like.

Specific conditions such as the number and positions of areas to be inspected that are selected in an object to be measured and the number of calcite particles required to calculate an average twin density may be appropriately determined in accordance with the purpose.

In the method described above, calcite particles, for which the initial value of the twin density is known (for example, zero), are mixed in concrete before placing the concrete, and a history of stresses received by an object to be measured is measured after the object to be measured, which has temporarily been elastically deformed upon receiving an external force, recovers from the elastic deformation. However, if sand-like calcite particles, for which the twin density is unknown, are contained in an existing concrete structure, for example, it is possible (i) to measure a stress event that may occur in the future, and (ii) to explore a local stress concentration inside the structure that occurred during a period from construction to the present.

Specifically, in the above case (i), it is considered that natural calcite particles have already experienced some stress event and thus already have twin crystals. The twin density in this state is acquired as an initial value, and the twin density is continuously measured to monitor an increase in twin density from the initial value due to a stress event.

In the above case (ii), assuming that the respective twin densities for the calcite particles are more or less constant in the entire structure, the structure can be evaluated by measuring an average twin density of a portion that is considered to have been subjected to a relatively low stress to determine the measured value as an initial value for the entire structure, finding a portion where calcite particles, for which the twin density is higher than the initial value, locally concentrate, and defining the portion thus found as the portion to be inspected.

Industrial Applicability

The present invention is suitable for application to a structure that is subjected to a stress at all times such as a dam and a power plant, a small bridge, a harbor breakwater, a small structure such as an apartment building, and so forth. In particular, the present invention is expected to be extremely useful to inspect whether a small structure keeps a predetermined strength after receiving a force that is no so large as to break the structure, for example a shake of an earthquake with an intensity of 5 plus or 6 which is never large enough to break the structure, to monitor a local stress concentration accompanied by deterioration of the structure itself, and so forth.

In addition, in evaluating the strength of a concrete structure, for example, in particular a reinforced concrete structure, the present invention allows measurement of the strength of concrete itself. Thus, it is expected that adequate evaluation can be made as to whether or not the arrangement of reinforcements is appropriate, whether or not the concrete material itself is appropriate, and so forth.

What is claimed is:

1. A method of measuring a stress history, comprising the steps of:
    acquiring an initial value of a twin density for calcite particles contained in an object to be measured that is elastically deformable upon receiving an external force; and
    measuring a history of stresses received by the object to be measured on the basis of a difference from the initial value in respect of the twin density for the calcite particles after the object to be measured receives the external force.

2. The method of measuring a stress history according to claim 1, wherein the twin density for the calcite particles is known and the calcite particles are mixed in advance to be distributed in the object to be measured.

3. The method of measuring a stress history according to claim 2, wherein the calcite particles mixed in advance in the object to be measured do not contain twin crystals.

4. The method of measuring a stress history according to claim 1, further comprising the steps of:
    defining at least one area of the object to be measured as an area to be inspected, and calculating an average value of the respective twin densities for a plurality of calcite particles each having a crystal face exposed on the area to be inspected to obtain an average twin density; and
    estimating the magnitude and distribution of the external force which has acted on the entire object to be measured on the basis of a difference between the initial value and the average twin density.

5. The method of measuring a stress history according to claim 2, further comprising the steps of:
    defining at least one area of the object to be measured as an area to be inspected, and calculating an average value of the respective twin densities for a plurality of calcite particles each having a crystal face exposed on the area to be inspected to obtain an average twin density; and
    estimating the magnitude and distribution of the external force which has acted on the entire object to be measured on the basis of a difference between the initial value and the average twin density.

6. The method of measuring a stress history according to claim 3, further comprising the steps of:
    defining at least one area of the object to be measured as an area to be inspected, and calculating an average value of the respective twin densities for a plurality of calcite particles each having a crystal face exposed on the area to be inspected to obtain an average twin density; and
    estimating the magnitude and distribution of the external force which has acted on the entire object to be measured on the basis of a difference between the initial value and the average twin density.

7. The method of measuring a stress history according to any one of claims 1 to 6, wherein the object to be measured is a composite material comprising:
    cement as a main component and
    calcite particles for which a twin density is known and which are mixed to be distributed in the material, partially replacing an aggregate of the material.

* * * * *